United States Patent
Mäki-Ikola et al.

(10) Patent No.: US 6,589,996 B2
(45) Date of Patent: Jul. 8, 2003

(54) TREATMENT OF DISORDERS RELATING TO THE SEROTONERGIC SYSTEM

(75) Inventors: Outi Mäki-Ikola, Turku (FI); Harri Kanerva, Lohja (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/809,327

(22) Filed: Mar. 16, 2001

(65) Prior Publication Data

US 2001/0049394 A1 Dec. 6, 2001

Related U.S. Application Data

(60) Provisional application No. 60/190,032, filed on Mar. 17, 2000.

(51) Int. Cl.$^7$ ............... A61K 31/54; A61K 31/495; A61K 31/445

(52) U.S. Cl. ............... 514/648; 514/645; 514/657; 514/661

(58) Field of Search ............... 514/644, 645, 514/657, 661

(56) References Cited

U.S. PATENT DOCUMENTS

| | | |
|---|---|---|
| 5,652,270 A | 7/1997 | Budai et al. |
| 6,093,747 A | 7/2000 | Gacsalyi et al. |
| 6,242,386 B1 | 6/2001 | Lukacs et al. |
| 6,335,371 B1 | 1/2002 | Maki-Ikola |
| 6,335,372 B1 | 1/2002 | Maki-Ikola et al. |
| 6,335,469 B1 | 1/2002 | Lukacs et al. |
| 2002/0040164 A1 | 4/2002 | Lukacs et al. |
| 2002/0132858 A1 | 9/2002 | Maki-Ikola et al. |

FOREIGN PATENT DOCUMENTS

| | | |
|---|---|---|
| WO | WO 98/17230 | 4/1998 |
| WO | WO 00/64441 | 11/2000 |
| WO | WO 01/41701 | 6/2001 |

OTHER PUBLICATIONS

Bojiti et al., "Pharmacokinetics of deramciclane in dogs", Pharmaceutical Sciences, vol. 3, pp. 503–506 (1997).

Csala et al., "Decrease of gluconeogenesis by deramciclane is counteracted by cytochrome P450 inhibitors", Pharmaceutical sciences, vol. 3, pp. 469–472 (1997).

Hazai et al., "Whole–body autoradiography and quantitative organ–level distribution study of deramciclane in rats", Jouranl of Pharmacy and Pharmacology, vol. 51, pp. 165–174 (1999).

Kanerva H., "Pharmacokinetic studies on deramciclane", Kuopio, Department of Pharmaceutics, University of Kuopio (1999).

Kanerva et al., "Pharmacokinetics of deramciclane in dogs after single oral and intravenous dosing and multiple oral dosing", Biopharmaceutics and Drug Disposition, vol. 19, pp. 531–539 (1998).

Kanerva et al., "Pharmacokinetics and safety of deramciclane during multiple dosing", Int. J. Pharmacol Ther., vol. 37 (12), pp. 589–597 (1999).

Kanerva et al., "Different absorption profiles of deramciclane in man and in dog", Journal of Pharmacy and Pharmacology, vol. 50, pp. 1087–1093 (1998).

Kanerva et al., "Brain 5–HT2A receptor occupancy of deramciclane in humans after a single oral administration—a positron emission tomography study", Psychopharmacology, vol. 145, pp. 76–81 (1999).

Klebovich et al., "Comparative pharmacokinetics of deramciclane in rat, dog, rabbit and man after the administration of a single oral dose of 3 mg kg–1", Pharm Pharmacol Commun., vol. 4, pp. 129–136 (1998).

Lengyel et al., "Pharmacokinetics of deramciclane in rabbits", Arzneimittel–Forschung, vol. 48 (II), pp. 1063–1068 (1998).

Lengyel et al., "Absorption of the new anxiolytic compound deramciclane in rats, dogs, and rabbits", Arzneimittel–Forschung, vol. 48 (I), pp. 455–460 (1998).

Magyar et al., "Distribution of deramciclane (EGIS–3886) in rat brain regions", European Journal of Drug Metabolism and Pharmacokinetics, vol. 23 (2), pp. 125–131 (1998).

Nemes et al., "Oral, intraperitoneal and intravenous pharmacokinetics of deramciclane and its N–desmethyl metabolite in the rat", Journal of Pharmacy and Pharmacology, vol. 52 (1), pp. 47–51 (2000).

Visy et al., "Plasma protein binding of deramciclane in different species", Pharmaceutical Sciences, vol. 2, pp. 315–318 (1996).

Visy et al., "Covalent protein binding of a minor deramciclane metabolite in dog plasma" Pharmaceutical and pharmacological commun., vol. 4, pp. 587–590 (1998).

Bilkei–Gorzo et al., "mCPP–induced anxiety in the light–dark box in rats—a new method for screening anxiolytic activity", Psychopharmacology (Berl), vol. 136, pp. 291–298 (1998).

Borden et al., "Cloning of the human homologue of the GABA transporter GAT-3 and identification of a novel inhibitor with selectivity for this site", Receptors and channels, vol. 2, pp. 207–213 (1994).

Détári et al., "Differential EEG effects of the anxiolytic drugs, deramciclane (EGIS–3886), ritanserin and chlordiazepoxide in rats", Psychopharmacology, vol. 142, pp. 318–326 (1999).

Gacsályi et al., "Different antagonist activity of deramciclane (EGIS–3886) on peripheral and central 5–HT2 receptors", Pharmaceutical and pharmacological letters, vol. 6 pp. 82–85 (1996).

(List continued on next page.)

Primary Examiner—Frederick Krass
(74) Attorney, Agent, or Firm—Finnegan, Henderson, Farabow, Garrett & Dunner, LLP

(57) ABSTRACT

A method for the treatment of disorders relating to serotonergic system in humans, for example depression and anxiety, comprising orally administering deramciclane in a daily dosage of about 20 to about 60 mg.

19 Claims, 2 Drawing Sheets

OTHER PUBLICATIONS

Gacsályi et al., "Psychopharmacology of a new anxiolytic agent Egyt–3886", Pharmacological research communications, vol. 20 (1), pp. 115–116 (1988).

Gacsályi et al., "Receptor binding profile and anxiolytic–type activity of deramciclane (EGIS–3886) in animal models", Drug development research, vol. 40, pp. 333–348 (1997).

Kõks et al., "8–OH–DPAT, but not deramciclane, antagonizes the anxiogenic–like action of paroxetine in an elevated plus–maze", Springer–Verlag (2001).

Kovács et al., "Inhibition of high–affinity synaptosomal uptake of gamma–aminobutyric acid a bicyclo–heptane derivative", Arzneim.–Forsch/Drugs Res., vol. 39 (3), pp. 295–297 (1989).

Kovács et al., "Inhibition of [3H]–D–aspartate relase by deramciclane", European journal of pharmcology, vol. 381, pp. 121–127 (1999).

Kovács et al., "Deramciclane inhibits N–methyl–D–aspartate receptor function", Brain research bulletin, vol. 52(1), pp. 39–44 (2000).

Pälvimäki et al., "Deramciclane, a putative anxiolytic drug, is a serotonin 5–HT2C receptor inverse agonist but fails to induce 5–HT2C receptor down–regulation", Psychopharmacology, vol. 136, pp. 99–104 (1998).

Varga et al., "Effect of deramciclane, a new 5–HT receptor antagonist, on cholescystokinin–induced changes in rat gastrointestinal function", European journal of pharmacology, vol. 367, pp. 315–323 (1999).

Hazai et al., "Application of TLC–digital autoradiography as a rapid method in pilot study of deramciclane metabolism", Journal of Planar Chromatography, vol. 8, pp. 92–97 (1995).

Klebovich et al., "A sensitive, validated Gas–chromatographic bioanalytical method by nitrogen selective detection of deramciclane in dog plasma", Pharmaceutical sciences, vol. 3, pp. 497–501 (1997).

Klebovich et al., "Isolation and identification of deramciclane metabolities by OPC–(DAR) on–line sample collection combined with MS techniques", Instrumental planar chromatography, Visegrád, Hungary, (1998), Research institute for medical plants.

Klebovich et al., "TLC–DAR for the analysis of biological samples. A newly developed rapid tool for studying drug metabolism", Journal of planar chromatography, vol. 10, pp. 399–405 (1997).

Ladányi et al., "Stereochemistry and enantiomeric purity of a novel anxiolytic agent, deramciclane fumarate", Chirality, vol. 11, pp. 689–693 (1999).

Ladányi et al., "Application of overpressured layer chromatography combined with digital autodiagraphy and mass spectrometry in the study of deramciclane metabolism", Journal of AOAC international, vol. 82 (2), pp. 231–238 (1999).

Nemes et al., "A highly sensitive GC method for the determination of deramciclane and its N–desmethyl metabolite in rat and dog plasma", Methodological surveys in bioanalysis of drugs, vol. 24, pp. 103–104 (1996).

Szammer et al., "Synthesis of deramciclane labelled with radiocarbon in various positions", Journal of labeled compounds and radiopharmaceuticals, vol. 39 (12), pp. 1011–1018 (1997).

Szúnyog et al., "Comparative Bioanalytical study of 3H–deramciclane in dog plasma, using a gas chromatography–nitrogen–selective detection (GC–NPD), a new GC–radiochemical detection (GC–RD) and a liquid scintillation method", Chromatographia, vol. 48 (1/2), pp. 133–139 (1998).

Szúnyog et al., "A new tool in planar chromatography: combination of OPLC and DAR for fast separation and detection of metabolities in biological samples", Journal of planar chromatography, vol. 11, pp. 25–29 (1998).

Takács–Novák, "Potentiometric pKa determination of water–insoluble compounds: validation study in methanol/water mixtures", International journal of pharmaceuticals, vol. 151, pp. 235–248 (1997).

Takács–Novák, "A deramciklán (EGIS–3886), agy ú anxiolitikum fizikai–kémiai tulajdonságainak vizsgálata. Ionizátició és lipofilitás", Acta pharmaceutica hungarica, vol. 69, pp. 123–127 (1999).

Tolokán et al., "Determination of deramciclane and N–desmethylderamciclane in human plasma by liquid chromatography–tandem mass spectrometry using off–line robotic sample pretreatment", Journal of chromatography, vol. 896, pp. 279–290 (2000).

Kanerva et al., "The Single Dose Pharmacokinetics and Safety of Deramciclane in Healthy Male Volunteers", Biopharm. Drug Dispos., vol. 20, pp. 327–334 (1999).

Giral et al., "Reversal of Helpless Behavior in Rats by Putative 5–HT $_{1A}$Agonists", Biol. Psychiatry, vol. 23, pp. 237–242 (1988).

Armer, "Inhibitors of Mammalian Central Nervous System Selective Amino Acid Transporters", Current Medicinal Chemistry, vol. 7, pp. 199–209 (2000).

EGYT–3886, "Drugs of the Future", vol. 15, pp. 1174–1175 (1990).

TREATMENT OF DISORDERS RELATING TO THE SEROTONERGIC SYSTEM

CROSS-REFERENCE TO RELATED APPLICATIONS

This application claims the benefit of priority under 35 U.S.C. §119(e) to U.S. provisional application No. 60/190,032, filed on Mar. 17, 2000, the contents of which are incorporated by reference herein.

FIELD OF THE INVENTION

An embodiment of the present invention is directed to the treatment of disorders relating to the serotonergic system with deramciclane, (1R,2S,4R)-(−)-2-[N,N-(dimethylaminoethoxy)]-2-phenyl-1,7,7-trimethyl-bicyclo[2.2.1]heptane, in humans.

Another embodiment of the present invention is directed to the treatment of depression with deramciclane in humans.

Another embodiment of the present invention is directed to the treatment of anxiety, for example, chronic anxiety, including generalized anxiety disorder (GAD), in an oral daily dosage of about 20 mg to about 60 mg in humans. The daily dosage may be given as a once-a-day formulation, or it may be divided. For example, a once-a-day formulation may be used, and may lead to greater patient compliance than a multiple-dose daily formulation.

BACKGROUND

The preparation of deramciclane as a free base and as a fumarate salt has been described in Hungarian Patent No. 212,547, the contents of which are incorporated by reference herein. Other pharmaceutically acceptable acid addition salts of deramciclane may be formed with inorganic (e.g., hydrochloric acid, sulfuric acid) or organic acids (e.g., acetic acid, tartaric acid). The fumarate salt is an example of such a pharmaceutically acceptable acid addition salt.

Deramciclane has shown anxiolytic-like effects in some conventional animal models with various routes of administration, and in receptor binding studies in vitro deramciclane has shown to bind with high affinity to serotonin $5HT_{2A}$- and $5-HT_{2C}$-receptor subtypes, being a potent antagonist of these receptors (Gacsalyi, I. et al., Drug Dv Res (1997) 40:333–348). In punished drinking tests in rats (Vogel, J. R. et al., Psychopharmacologia (1971) 21:1–7) deramciclane was active, after single oral administration at doses of 1 mg/kg and 10 mg/kg. In social interaction tests in rats (File, S. E. J. Neurosci Methods (1980) 2:219–238) deramciclane enhanced the social interaction time, and the minimum effective dose after single intraperitoneal administration was 0.7 mg/kg. In two compartment tests in mice (Crawley, J. and F. K. Goodwin, Pharmacol Biochem Behav. (1980) 13, 167–170. & Crawley, J. N., Pharmacol. Biochem. and Behav. (1981) 15,695–699) deramciclane was active after single subcutaneous administration at a dose of 3 mg/kg. In marble-burying test in mice (Broekkamp, C. L. et al., Eur J. Pharmacol. (1986) 126:223–229) the effective doses were 10 mg/kg and 30 mg/kg orally. Nevertheless, deramciclane was totally ineffective in elevated plus maze test in rats (Handley, S. L. and S. Mithani, 1984, Effects of Alpha-Adrenoceptor Agonists and Antagonists in a Maze-Exploration Model of "Fear"-Motivated Behaviour, Naunyn-Schmiedeberg's Archives of Pharmacology. 327, 1–5) after single intraperitoneal doses at a range of 0.1 mg/kg–5 mg/kg. However, deramciclane was able to attenuate the caerulein-induced decrease in exploratory behavior at an intraperitoneal dose of 0.5 mg/kg in the elevated plus maze test.

The possible antidepressant activity of deramciclane has also been evaluated in various conventional animal models (Gacsalyi, I. Et al, Drug Rv. Res. (1997) 40:333–348). In learned helplessness tests in rats (Giral et al. Reversal of helpless behavior in rats by putative 5-HT1A agonists. Biol. psychiatry 23: 237–242), deramciclane dose dependently attenuated helpless behaviour induced by inescapable electric foot shocks, when given intraperitoneally 1 or 10 mg/kg, repeatedly 8 times, twice a day, before the test. The effect of deramciclane was found to be negligible, even at relatively high oral doses, 48–160 mg/kg, when evaluated for tetrabenazine-induced ptosis in mice according to the method of Howard et al. (Howard, J. L. et al., (1981) Empirical behavioral models of depression with emphasis on tetrabenazine antagonism. In Enna S. J., Malick J. B., Richelson E. (eds.): Antidepressants: Neurochemical, Behavioral, and Clinical Perspectives. New York: Raven Press, p 107). In the forced swimming test in rats (Porsolt R. D. et al., Eur. J. Pharmacol. (1978) 47:379–391) deramciclane was clearly ineffective at oral doses of 25 and 100 mg/kg.

Thus, deramciclane has been effective in some animal models of anxiety after oral doses in a range from 1 mg/kg to 30 mg/kg in mice and rats. Further, deramciclane has shown negligible effects in animal models of depression even after high peroral doses in mice and rats, which is in line with the results reporting that $5-HT_{2C}$-receptor agonists are effective in animal models of depression (Moreau J-L. et al. European Neuropsychopharmacology 6:169–175, 1996).

In a whole body autoradiography distribution study with tritium labeled deramciclane in rats (Hazai, I, et al. J. Pharm. Pharmacol. 51: 165–174, 1999) at a dose of 3 mg/kg, it was found that after intravenous administration there was high radioactivity (reflecting amount of deramciclane) in several organs including blood and the brain, but after oral administration the amount was substantially lower, especially in the brain.

In a comparative pharmacokinetic study of orally administered deramciclane in rats, dogs, rabbits and humans (Klebovich et al Pharm. Pharmacol. Commun., 4:129–136, 1998), it was shown that the plasma concentration curves obtained after the administration of a single 3 mg/kg oral dose of deramciclane to rats (dogs, rabbits) and human show considerable species specific differences. In the peak plasma concentration (Cmax) values there were significant differences: Cmax was 5.4 ng/ml in rat and 217.5 ng/ml in human after the same 3 mg/kg oral dose. Thus a 40-times lower oral dose of deramciclane could be used in man to result in the same maximal plasma concentration as in rat. Furthermore, the total amount of deramciclane absorbed into blood, calculated as Area Under Curve values (AUC 0-∞) from plasma concentrations as a function of time, showed more considerable species difference. The mean AUC 0-∞ values after single oral administration of deramciclane were 11.9 ng h/ml and 3737.8 ng h/ml in rat and human, respectively. Thus, over 300 times lower oral doses should result in equal exposure in humans than in rats. Basing only the Cmax difference between rat and man, it can be predicted that considerably lower doses should be centrally active in humans than in rat. The minimum oral effective anti-anxiety dose in rats was 1 mg/kg (1–30 mg/kg the full range; see above), i.e. in a 70 kg-man this would mean 70 mg dose. To reach the same pharmacologically active plasma concentration in humans as was shown to be efficacious in rat, one should divide the rat dose by 40. This would result in 70 mg/40=1.75 mg (i.e. 0.025 mg/kg) as an effective dose in man.

The binding of deramciclane to serotonin 5-HT$_{2A}$-receptors in frontal cortex of healthy male volunteers after a single oral dose of 20, 50 and 150 mg of deramciclane is discussed in Kanerva, H. et al., Psychopharmacology (1999) 145:76–81. The determination of the brain 5HT$_{2A}$-receptor occupancy of deramciclane in humans has shown that 90% and 50% receptor occupancies were reached at a deramciclane plasma concentration of about 70 ng/ml and 21 ng/ml, respectively. The pharmacokinetics of a single dose of deramciclane and during oral dosing of 10 mg, 30 mg and 60 mg twice a day for seven days are discussed in Kanerva, H., Pharmacokinetic studies on deramciclane. Kuopio University Publications A. Pharmaceutical Sciences 39.1999. After a single oral administration of 20 mg and 30 mg doses of deramciclane, the Cmax-values were 24±9.4 ng/ml and 27±6.1 ng/ml, respectively. During repeated administration of deramciclane for one week the Cmin and Cmax for 60 mg and 20 mg daily doses were shown to range between 48–91 ng/ml and 16–33 ng/ml, respectively.

As the above experimental animal and human data does not disclose repeated administration of deramciclane rendering steady state plasma concentrations in treated patients, it was impossible to predict the oral dosages of deramciclane that would be effective in treating anxiety in humans. Furthermore, it was totally unexpected that deramciclane would be effective in treating depressive symptoms.

Anxiety is a normal emotional feeling related to different situations of threat or fear. External threat is experienced as a fear whereas obscure and unidentified feeling of threat may be experienced as anxiety. When anxiety persists it can develop into a pathological disorder. Anxiety disorders are divided more specifically in diagnostic disorders e.g., panic disorder, phobias, and GAD. GAD is a chronic illness associated with excessive anxiety and worry lasting for at least six months. In addition, the anxiety and worry are associated with restlessness, fatigue, difficulties in concentrating or mind going blank, irritability, muscle tension, and sleeping disturbances. The symptoms may be triggered by different events of life, and the control of anxiety is very difficult for the patient.

Anxiety is currently treated with benzodiazepines, SSRI's and buspirone, which are not optimal treatments due to adverse drug reactions and their efficacy profiles. Moreover, relapse of the disease, different kinds of withdrawal effects, development of tolerance, as well as relapse and recurrence, often happen when traditional anxiolytics are used. For example, to avoid withdrawal effects, doctors usually gradually taper the dosage of the medicine (i.e. gradually diminish its daily dosage) before the treatment may be stopped. Patients tend to develop tolerance to those traditional compounds as well. Development of tolerance occurs when, for example, a patient requires greater quantities of a compound over time to achieve the same therapeutic effect.

In the treatment of psychiatric disorders with a chronic course, such as anxiety, it is important to prevent the relapse and recurrence of the disease. After the acute treatment phase, the improved condition can be maintained, and relapses can thus be prevented by continuing the treatment in those who have responded to the treatment or who have reached remission during it. After the continuation treatment phase, when recovery has been reached, the disease can be prevented by continuing the treatment further by the so-called maintenance treatment, during which the daily dosage may be decreased, for example, to a half from the original.

There has thus been a long felt need in the art to obtain an anxiolytic medicament, which is void of withdrawal and discontinuation effects and does not cause development of tolerance in patients. Furthermore, sufficient efficacy in relapse and recurrence prevention are important qualities of a well functioning anxiolytic drug. It is believed that deramciclane satisfies this need in the art.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

Figure 1:
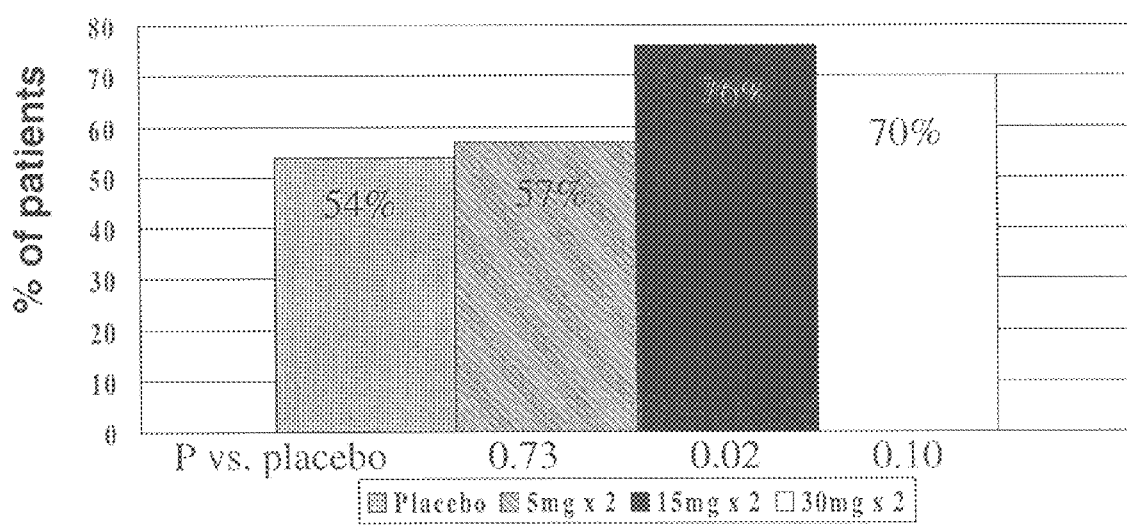
FIG. 1 shows the number of responders (at least 50% reduction in HAM-A scale) in the treatment of anxiety.

An embodiment of the present invention is directed to a method of treating a disorder of the serotonergic system in a human, which comprises administering to the human in need of the treatment an oral daily dosage of about 20 mg to about 60 mg of deramciclane. For example, the invention includes administering a daily dosage of deramciclane of about 30 mg to about 60 mg, or about 20 mg to about 40 mg, or about 30 mg.

One disorder of the serotonergic system treatable according to the present invention is anxiety, for example chronic anxiety. The present invention also includes the treatment of GAD. Another embodiment of the invention is directed to a treatment of chronic anxiety where the patient does not experience relapse of the disorder.

Another embodiment of the invention is directed to a method of treating depression in a human, which comprises administering to the human in need of the treatment a therapeutically effective amount of deramciclane, for example, an oral dosage of about 20 mg to about 60 mg, or about 30 mg to about 60 mg, or about 20 mg to about 40 mg, or about 30 mg.

It is a further object of the invention to provide a treatment regimen of deramciclane that does not require, to avoid withdrawal effects, diminishing the treatment dosage before terminating treatment. In other words, in this embodiment, the patient may continue receiving the full treatment dosage up to the point of termination of treatment, and will not suffer withdrawal effects that would have otherwise followed using other conventional treatments. In an embodiment of the invention, a standard daily dosage of deramciclane is given to the patient for a period long enough, for example from three weeks to ten years, or from two months to five years, or from eight months to two years, to cause relief of the symptoms, whereafter the treatment is abruptly terminated. By "abruptly terminated" it is meant that the dose is decreased within 24 hours from the standard dosage to less than a fourth of the standard dose, for example, to zero.

Another embodiment of the invention is directed to the above-described methods of treatment, which comprise administering deramciclane in a once-a-day formulation.

A dosage of about 30 mg of deramciclane may be used, for example, in a conventional relatively fast release formulation. When the corresponding slow release formulation is used, the dosage may be about 20 mg to about 40 mg, for example about 20 mg.

In the present invention it has been discovered that when treating disorders relating to anxiety in humans with deramciclane, an effective clinical response was obtained with an oral dosage amount of, for example, 30 mg–60 mg/day. When deramciclane was used in the treatment of anxiety, specifically GAD, the oral dosage amount of 30–60 mg/day, for example, was found to be effective in Hamilton Anxiety Scale (HAM-A) and in Clinical Global Impression (GCI) scale.

In addition, in the present invention it has been discovered that deramciclane is effective in treating depressive disorders in humans. Specifically, the same oral dosage amount of 30–60 mg/day, for example, which was effective in the treatment of anxiety was found to be effective on the depressive symptoms in the Montgomery Asberg Depression Rating Scale (MADRS).

The oral dosage amount of deramciclane in the methods of the present invention can be divided into two or more daily doses or can be administered once on a daily basis.

Use of the term "about" with respect to the dosage amounts includes the natural industry variation in dosage amounts of drugs administered to patients. For example, a variation of ±5% in a given dosage amount in the methods of the present invention would be included by the term "about" in the present invention. For example, a dosage of 30 mg ±5% is included within the phrase "about 30 mg" in an embodiment of the present invention.

EXAMPLE

The efficacy of deramciclane in the treatment of anxiety, specifically GAD, was studied in a randomised placebo-controlled double-blind study. In addition, the dosage-dependency of the effects of deramciclane was evaluated. A total of 208 patients were included in the study. The subjects were randomly assigned to four parallel groups to receive one tablet twice daily (b.i.d) of a placebo, 5 mg (=10 mg/day), 15 mg (=30 mg/day), or 30 mg (=60mg/day) deramciclane. The study started with a one-week placebo run-in period, followed by an eight-week placebo-controlled active treatment and a two-week placebo washout period.

The efficacy of deramciclane on anxiety symptoms was studied by the efficacy variable Hamilton Anxiety Scale (HAM-A), analyzing the change in the score and using responder criterion (at least 50% reduction in HAM-A total score). The Clinical Global Impression (GCI) scale was also used for analyzing the efficacy of deramciclane on anxiety symptoms.

The efficacy of deramciclane on depressive symptoms was studied using the Montgomery Asberg Depression Rating Scale (MADRS).

Results

Anxiety

The HAM-A score decreased 14.5 points from baseline in groups receiving either 15 mg b.i.d or 30 mg b.i.d. dosage. However, only the 15 mg b.i.d group differed statistically significantly from placebo (p=0.006). No difference was found between the 5 mg b.i.d and placebo.

The number of responders (at least 50% reduction in HAM-A scale) is presented in FIG. 1. The responder criterion was reached by 54% (n—27), 57% (n=31), 76% (n=39) and 70% (n=37) of patients on placebo, 5 mg, 15 mg and 30 mg b.i.d. dosing, respectively. In comparison, between the deramciclane dosage levels and placebo, only 15 mg b.i.d. was statistically better than placebo (p=0.020).

Figure 2:
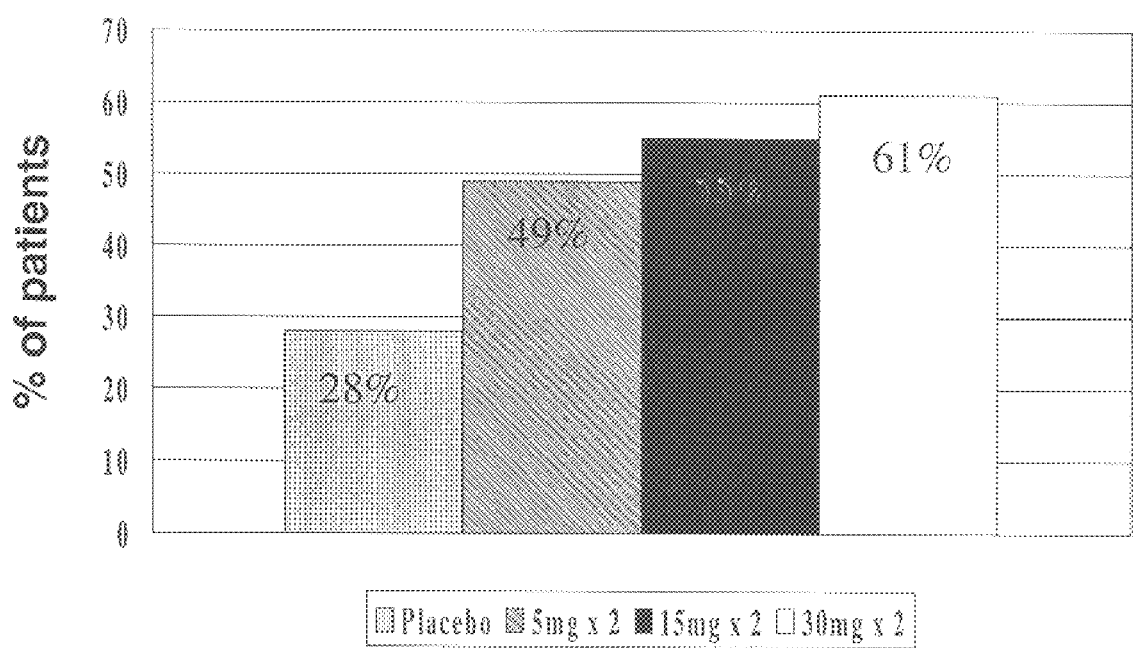
FIG. 2 shows the results of CGI of severity of illness rating after 8 weeks of treatment for anxiety.

The results of CGI of severity of illness rating after 8 weeks of treatment are shown in FIG. 2. The percentage of patients who were either not ill or very mildly ill is higher in deramciclane treated patients (placebo 28%, 5 mg b.i.d 49%, 15 mg b.i.d 55% and 30 mg b.i.d 61%). Using the correlation statistic model, 30 mg b.i.d. was the only dosage where a statistically significant improvement in CGI (p=0.030) was observed at the end of the active treatment.

Lack of Withdrawal Symptoms

After stopping the above-described 8-week treatment period, no discontinuation effects were seen (measured by the Physician's Withdrawal Checklist, PWC). This is different and surprising from the experiences with the most other efficacious drugs used for the treatment of anxiety.

TABLE 1

The PWC values at 8 weeks (when the treatment was stopped) and at 10 weeks (after a two week wash out period)

| Dosage | After 8 week treatment | After 2 week wash-out |
| --- | --- | --- |
| Placebo | 12 (10) | 12 (11) |
| 5 mg b.i.d. deramciclane | 9 (7) | 9 (8) |
| 15 mg b.i.d. deramciclane | 7 (8) | 8 (7) |
| 30 mg b.i.d. deramciclane | 8 (8) | 8 (7) |

Mean (SD)

Thus, deramciclane did not cause any withdrawal symptoms after abrupt discontinuation of the treatment. Therefore, it may be used as a treatment for serotonergic diseases without any withdrawal effects.

Depression

MADRS scores decreased similarly and statistically significantly in both 15 mg b.i.d and 30 mg b.i.d groups (7.7 and 8.0 points, p=0.028 and 0.016, respectively). 5 mg b.i.d dosage was ineffective. Thus, both the oral daily dosages of 30 mg and 60 mg of deramciclane were found to be effective on the depressive symptoms.

Although the invention has been illustrated by the preceding example, it is not to be construed as being limited to the materials employed therein; rather, the invention is directed to the generic area as herein disclosed. Various modifications and embodiments thereof can be made without departing from the spirit or scope thereof.

We claim:

1. A method of treating anxiety in a human, which comprises administering to a human in need of the treatment an oral daily dosage of about 20 mg to about 60 mg of deramciclane.

2. A method according to claim 1, wherein the anxiety is chronic.

3. A method according to claim 2, wherein the patient does not experience relapse of the anxiety.

4. A method according to claim 1, wherein the anxiety is generalized anxiety disorder.

5. A method according to claim 1, wherein the daily dosage of deramciclane is about 30 mg to about 60 mg.

6. A method according to claim 1, wherein the daily dosage of deramciclane is about 30 mg.

7. A method according to claim 1, wherein the daily dosage of deramciclane is about 20 mg to about 40 mg.

8. A method according to claim 1, which comprises administering the deramciclane in a once-a-day formulation.

9. A method of treating depression in a human, which comprises administering to a human in need of the treatment a therapeutically effective amount of deramciclane.

10. A method according to claim 9, wherein the deramciclane is administered orally.

11. A method according to claim 10, which comprises administering a daily dosage of about 20 mg to about 60 mg of deramciclane.

12. A method according to claim 10, which comprises administering about 30 mg to about 60 mg of deramciclane.

13. A method according to claim 10, which comprises administering about 30 mg of deramciclane.

14. A method according to claim 10, which comprises administering about 20 mg to about 40 mg of deramciclane.

15. A method according to claim 10, which comprises administering the deramciclane in a once-a-day formulation.

16. A method of treating anxiety in a human, which comprises administering to a human in need of the treatment a daily dosage of deramciclane to treat the anxiety, and Then abruptly terminating the treatment.

17. A method according to claim 16, wherein the daily dosage is given to the patient for at least three weeks.

18. A method according to claim 16, wherein the daily dosage is about 20 to about 60 mg.

19. A method according to claim 17, wherein the daily dosage is about 20 to about 60 mg.

* * * * *